United States Patent [19]

Shen

[11] Patent Number: 5,911,000
[45] Date of Patent: Jun. 8, 1999

[54] DETECTING ABNORMAL REACTIONS IN A RED BLOOD CELL AGGLUTINATION

[75] Inventor: Jian Shen, Princeton, N.J.

[73] Assignee: Ortho Diagnostic Systems, Inc., Raritan, N.J.

[21] Appl. No.: 08/904,506

[22] Filed: Aug. 1, 1997

[51] Int. Cl.⁶ ..................................................... G06K 9/00
[52] U.S. Cl. ............................................. 382/134; 422/73
[58] Field of Search .................................... 382/128, 129, 382/133, 134; 356/39; 422/73; 128/922; 73/61.69, 64.43

[56] References Cited

U.S. PATENT DOCUMENTS

| 4,563,430 | 1/1986 | Kano et al. | 436/164 |
| 5,225,350 | 7/1993 | Watanabe et al. | 436/165 |
| 5,389,555 | 2/1995 | Watanabe et al. | 436/164 |
| 5,594,808 | 1/1997 | Shen et al. | 382/133 |

Primary Examiner—Andrew W. Johns
Attorney, Agent, or Firm—Dana M. Schmidt

[57] ABSTRACT

Abnormal reactions in a red blood cell classification by agglutination, are checked following centrifugation of a sample in a column of a cassette, the column containing microparticles. This is done by imaging the column on a detector array that is used to correlate the images with predefined red cell classes based upon the distribution of the images across the column. However, prior to the correlation step, abnormal reactions are checked for by detecting whether any of the following is present:
  i) errors that cause imaged features of the column or any pellet produced therein to be out of range;
  ii) hemolysis of the sample;
  iii) insufficient or too many blood cells present;
  iv) mixed field agglutination; and
  v) presence of fibrin at the top of the microparticles.

11 Claims, 6 Drawing Sheets

COMPARATIVE EXAMPLE

DETECTING ABNORMAL REACTIONS IN A RED BLOOD CELL AGGLUTINATION

FIELD OF THE INVENTION

This invention relates to the field of detection and quantification of agglutinates for red blood cell classification, and more particularly, to a method for detecting and flagging the most common abnormal reactions that can interfere with a proper classification based upon agglutinations. In addition, some of these reactions yield important diagnostic information in themselves.

BACKGROUND OF THE INVENTION

Immunological agglutination reactions are used for identifying blood types and detecting various antibodies and antigens in blood samples and other aqueous medium.

In a conventional procedure, particles with binding agents, such as red blood cells, are mixed with a sample or reagent in test tubes or microtiter plates, and the mixture may then be incubated and centrifuged. Various reactions either occur or do not occur depending on antigens or antibodies present in the particle surface and reagent sample. Typically, these reactions manifest themselves as clumps of cells or particles, referred to as agglutinates. Thus, the absence of such clumps indicates that no reaction has occurred; and the presence of such clumps indicates that a reaction has occurred, with the size and amount of such clumps being a semi-quantitative indicator of the level or concentration of antigens or antibodies in the sample, or an indicator of the reaction strength, affinity of the complex for which the blood sample was tested.

Recently, a new agglutination assay, referred to as column agglutination technology (CAT), has been developed. This agglutination testing method utilizes filtration as a means of separating agglutinated particles from non-reactive components for immunoassay applications. In this method, gel or glass bead microparticles are contained in a small column, referred to as microcolumn, along with a reagent such as Anti-IgG. Red blood cells, or particles with binding agents, are placed in a reaction chamber above the column. During centrifugation, the cells or particles are mixed with reagent and may react in the column. If the reaction occurs, part or all of the cells are agglutinated and trapped in the bead area after centrifugation. If the reaction does not occur, the non-agglutinated cells are forced toward the bottom of the column by the centrifugal force. As a result, the nature and distribution of the particles in the microcolumn after centrifugation provides a visual indication of whether any reaction occurred, and if so, of the strength of the reaction.

Conventionally, an agglutination reaction is classified as negative (if no reaction occurred) or as positive (if a reaction has occurred) and if positive, the reaction is further classified as a class of +0.5, +1, +2, +3 or +4, depending on the strength of the antigen-antibody interaction. Indeterminate reaction is given if the nature of the reaction cannot be surely classified. In the CAT method, the classes of agglutination reactions can be determined on the basis of red cell distribution pattern in the microcolumn.

In U.S. Pat. No. 5,594,808, there is disclosed a system and software for automatically classifying the types of agglutinate reactions described in the previous paragraph, referred to as normal reactions. That system and software works well in most instances. Occasionally, however, there are other types of immunological reactions with red blood cells, which are considered abnormal for the purposes of this invention. These include:

Hemolysis reaction: In a hemolysis reaction, part or all of red blood cells are broken (hemolyzed) due to the antigen-antibody reaction. Once the cells are broken, the hemoglobin in the red blood cells are released into the test sample, resulting in the change of liquid color to red.

Mixed field reaction: In a mixed field reaction, part of red blood cells are agglutinated while the remaining red cells do not agglutinate. This may indicate that the test sample contains two different population of red cells, which may be caused by a previous transfusion or other pathological conditions.

These reactions and other abnormalities can interfere with detection by the system and software described in the aforesaid '808 patent.

SUMMARY OF THE INVENTION

I have devised a method for dealing with the aforesaid abnormalities, and others, that interfere with the detection described in the '808 patent.

More specifically, there is provided a method for detecting abnormal reactions in a cassette used for classifying red blood cell agglutination, the method comprising the steps of:

a) inserting a patient blood sample into a cassette provided with agglutinating reagents and a column of microparticles;

b) centrifuging the cassette to force non-agglutinated blood cells to flow through the column while retaining agglutinated cells at indicative locations in the column;

c) producing on a detector array comprising a plurality of pixels, an image of the column and of blood cells distributed within and around the column;

d) correlating the image on the array with predefined classes of images representing agglutination reactions of known classes; and e) prior to the step d), detecting the existence if any of an abnormality in the produced image selected from the group consisting of:

i) errors in the processing of steps a), b), or c) that cause imaged features of the column or any pellet produced in the column to be out of range;

ii) hemolysis of the sample inserted in the step a);

iii) insufficient or too many blood cells present in the cassette;

iv) mixed field agglutination; and v) presence of fibrin at the top of the microparticles.

As a result of this method, it is possible to halt the process prior to the correlation step d) noted above, and if desired, repeat the entire process on a fresh aliquot of the sample.

Therefore, it is an advantageous feature of the invention that the chances of the reaction classification routine of the '808 patent being falsified by the presence of the noted abnormalities is reduced.

An additional advantageous feature is that an abnormality useful in diagnosis can be detected and used as a result.

Other advantageous features will become apparent in light of the following Detailed Description when read in light of the attached drawings.

DESCRIPTION OF THE PREFERRED EMBODIMENTS

The invention is hereinafter described in connection with certain preferred embodiments, which utilize a cassette of a particular shape and composition, containing preferred reagents, and which is processed to classify red blood cell agglutinations into certain preferred classes following centrifugation. In addition, the invention is useful regardless of the shape or composition of the cassette or the reagents therein, or the classes of normal agglutination that are used following centrifugation, provided that the columns or containers of the cassette have regions corresponding to those identified herein so as to fit the algorithms used herein to flag the noted abnormalities.

U.S. Pat. No. 5,594,808 discloses a preferred processing system and cassette for carrying out this invention, and those portions thereof not expressly disclosed herein are incorporated herein by reference. As explained in the '808 patent, the preferred automated optical reading system 10 comprises, generally, holding means 12, illumination means 14, imaging subsystem 16, and processing subsystem 20; and preferably system 10 further includes transport subsystem 22, storage means 24, waste receptacle 26, and bar code reader 30. With the embodiment of system 10 shown in FIG. 1, holding means 12 includes base 32 and frame 34; and illumination means 14 includes a pair of fluorescence lights, and diffuser, not shown. Imaging subsystem 16 includes pixel array 42, housing 44, and lens assembly 46. Also, the preferred processing subsystem 20 includes preprocessor 56, main processor 60, and input means such as keyboard 62; and the preferred transport subsystem 22 shown in FIG. 1 includes support means 64 and mover 66.

Figure 1:
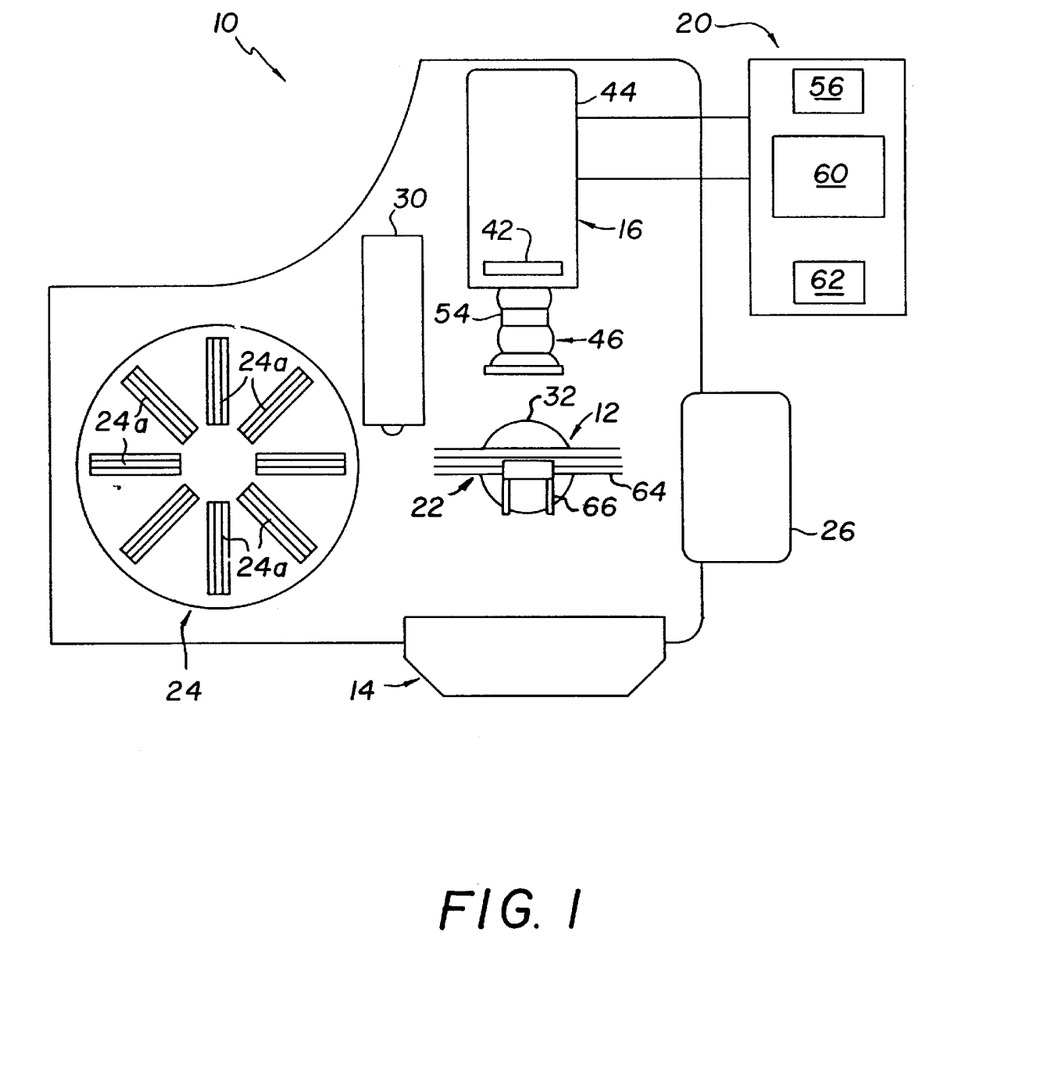
FIG. 1 is a schematic diagram of an automated blood analysis system used in the present invention.

Generally, holding means 12 is provided to hold a test sample for analysis, and illumination means 14 is provided to produce an illuminated image of the test sample on imaging subsystem 16. Subsystem 16 generates a set of signals representing the illuminated image formed thereon and then transmits those signals to processing subsystem 20. The processing subsystem receives those signals from subsystem 16 and processes those signals according to a predetermined program to determine whether an agglutination pattern is present in a test sample being analyzed and, if so, to classify that pattern in one of a plurality of predefined classes.

The preferred embodiment of system 10 described herein is particularly well suited for analyzing blood samples, and these samples are often referred to as solutions. It should be noted that the present invention may be embodied in systems that analyze other materials, including other aqueous solutions such as urine. It is not necessary, though, that the material being analyzed be a liquid or a fluid; and, thus, the term "solution" as used herein is used in the general sense as any mixture of liquid, or solid substances.

In addition, the test samples analyzed in system 10 are preferably held within containers, and a large variety of types and sizes of containers may be used with system 10. However, the preferred embodiment of system 10 described herein in detail is particularly well suited for use with cassette containers of the type shown at 80 in FIGS. 2 and 3. These containers, referred to hereinafter as cassettes, are made from a transparent, integrally molded plastic material. A multitude of cavities or wells 82, FIG. 2, referred to as columns or microcolumns, are formed in the cassettes and extend downward from the top edge 84 of the cassette, and, for example, the cassette shown in FIGS. 2 and 3 contains six such microcolumns.

Figure 2:
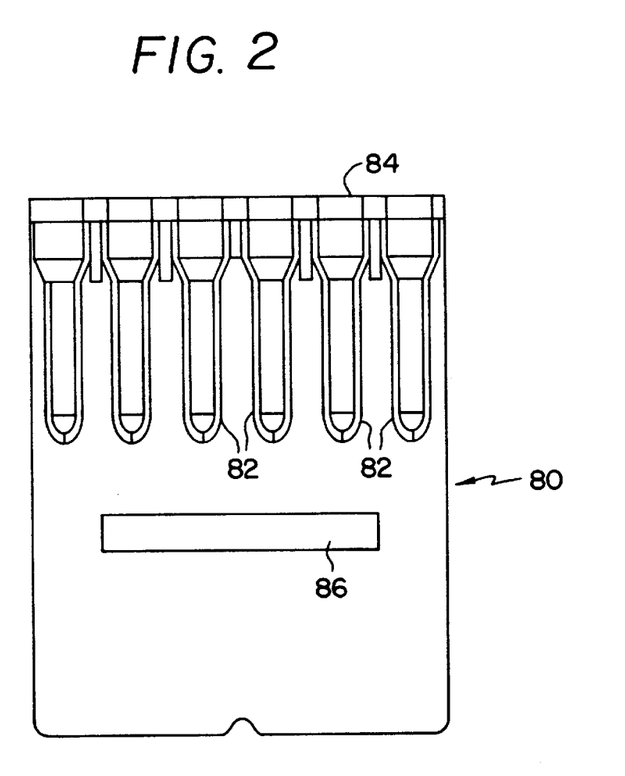
FIGS. 2 and 3 are front and side elevational views of a cassette useful in the present invention.
Figure 3:
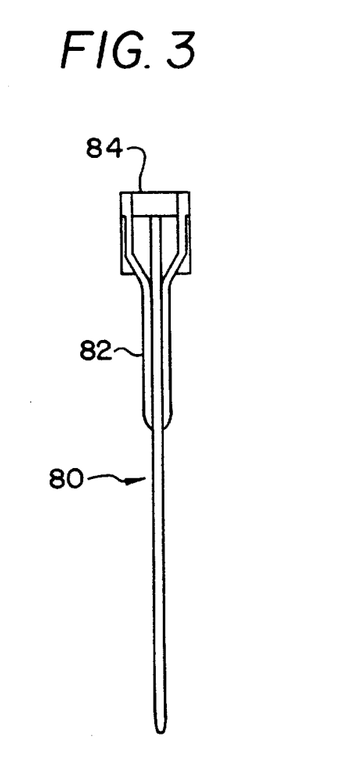

A multitude of very small, transparent glass beads 90, having diameters on the order of magnitude of 10 to 100 micrometers, are deposited in and form a filter in the lower portion of each microcolumn. Alternately, the lower portion of each microcolumn may be provided with a suitable gel that functions in the same general way as the microparticles. Reagents may be pre-dispensed in the columns of the cassette; and after the columns of the cassette are provided with the desired materials, a foil is typically secured on the top edge 84 of the cassette to cover and close the tops of columns 82.

When any particular cassette 80 is used, one, some, or all of the microcolumns 82 in the cassette may be used. Moreover, each cassette may be used with blood samples from one or more individuals. In each microcolumn that is used, a sample of red blood cells and one or more reagents that react with known agents are pipetted into the microcolumn to test that blood sample for the presence of that one or more agents. The cassette may be incubated and is then centrifuged. If an agent, for which the blood sample is being tested, is present in the microcolumn, the agent reacts with the red blood cells to form agglutinates; and the number, size, and distribution of the agglutinates in the microcolumn is an indication of the strength of that reaction.

With reference again to FIG. 1, illumination means 14, which preferably comprises a pair of fluorescence lamps, directs light through the test sample held by mover 66 and onto imaging subsystem 16, and specifically onto pixel array 42, which then generates a series of signals representing the test sample. More particularly, pixel array 42 is disposed inside a camera housing 44, and the pixel array is preferably comprised of a multitude of light sensors each of which is capable of generating a respective one electric current having a magnitude proportional to or representing the intensity of light incident on that sensor. Preferably, these light sensors, or pixels, are arranged in a uniform grid of a given number of uniformly spaced rows and columns.

As will be understood by those of ordinary skill in the art, any suitable light source 14, lens, filter, and camera 44 may be used in system 10. For example, in an embodiment of system 10 that has been actually reduced to practice, camera 44 is a Sony XC-75CE video camera, and the pixel array or sensoring element in this camera is a charged coupled device (CCD) comprising a matrix of pixels in a rectangular array, 752 pixels by 582 pixels. The distance between the camera and the cassette held in frame 34 was adjusted so that each image on the pixel array contains two columns 82 of the cassette, and the width of each column in the image is about 140 pixels.

A Componon microlens manufactured by Schneider Corporation was set at an F stop of F/4.0 and attached on the camera via an adapter. Between the lens and the CCD element was fixed a band pass filter with a center wavelength of 550 nm and a band width of 40 nm. This filter enhances the image of the red cells and improves the signal to noise ratio, and the filter was selected on the basis of a spectrophotometer measurement, which indicates that red blood cells have increased absorption of light in the corresponding wavelength range.

As explained in greater detail in the '808 patent, processor 60 is programmed to process and to analyze the data values stored in the image processor to identify the agglutination pattern, if any, in the test sample being analyzed.

Preferably, main processor is, or is a component of, a personal computer also having keyboard 62 and a terminal (not shown). Keyboard 62 is connected to processor 60 to allow operator input thereto, and terminal is used to display visually data or messages being input into the processor. In addition, a monitor may be connected to processor 56 to produce video images from the data value stored in the processor or in image processor 56. For example, the S data values may be transmitted to the monitor to produce thereon an image of the real image produced on pixel array 42. Other sets of data values may be transmitted to the monitor to produce refined or processes images of the real image. A printer may be connected to processor 60 to provide a visual, permanent record of selected data values transmitted to the printer from the processor.

As will be understood by those of ordinary skill in the art, subsystem 20 may be provided with other or additional input or output devices to allow an operator or analyst to interact with processors 56 and 60. Also, the individual components of subsystem 20 are conventional and well-known by those of ordinary skill in the art.

Storage means 24 is located adjacent holding means 12 and is provided for holding a multitude of test samples, and preferably indexing means such as a stepper motor is provided for moving the storage means through a series of positions to align each of the test samples held therein with the holding means. The storage means 24 shown in FIG. 1 is particularly designed for holding cassettes 80, and the storage means forms a multitude of channels or slots 24a for holding those cassettes. The indexing means moves this storage means 24 so as to align each of the channels 24a with the cassette mover 66, allowing the cassettes to be slid from the storage means and into that frame.

Preferably, each cassette 80 is provided with a bar code 86 identifying selected data about the cassette, and bar code reader 30 is provided to read the bar code on each cassette and to transmit the data thereon to processor 60. For example, the bar code on the cassette may identify the cassette type, the date of manufacture of the cassette, and a recommended expiration date for the cassette. The bar code may include other data that identify the cassette manufacturer as well as the time and place of manufacture. As shown in FIG. 1, the code reader, which may be a standard bar code reader, is preferably located between storage rack 24 and mover 66 so that the reader scans the bar code on each cassette as the cassette is being transferred from the storage rack to a position in front of pixel array 42. As an option, if the bar code 86 does not properly identify all the selected data, system 10 may be operated so that there is no processing of any image data from the cassette 80. For example, this may be done by not producing any image of the cassette on pixel array 42, or if an image is produced, by not processing that image.

In the operation of system 10, a multitude of test samples are placed in carousel 24, and the carousel is rotated to align a selected one of the slots 24a with mover 66. Then, mover 66 slides the test sample in that selected carousel slot, into the desired position in front of pixel array 42, and illumination means 14 then directs a beam of light through the test sample and onto pixel array 42. Mover 66 is rotated by its base 32 to allow the opposite side of the cassette to be imaged. Positioning of the cassette is determined by detecting the position of the columns. No separate positioning marks are needed.

Other processing details can be found in the '808 patent.

Normal agglutination reactions fall into the following types of reactions—negative, positive (+0.5, +1, +2, +3, +4) and indeterminate reactions. As disclosed in the '808 patent, the procedure of reading a reaction include steps of image acquisition, column detection, feature extraction and reaction grading. After the completion of the feature extraction by the image processing routine, the set of features related to the reaction pattern are calculated for each column. These features, along with the intensity reference values, are inputted to a reaction classification program (classifier) and the reaction classifier translates these feature values into one of reaction classes noted above.

THE INVENTION

The problem is, there are abnormal reactions that can prevent the system and software of the '808 patent from achieving the noted classification. These include the abnormal reactions or conditions noted above in the Background and Summary. To deal with those abnormal reactions, certain terms have been identified, particularly those associated with the columns 82 of the cassette 80. These terms and their location relative to the cassette are set forth below in Table 1:

TABLE 1

| Term | Definition |
| --- | --- |
| Above | Mean light intensity in a predefined area in the clear liquid portion 92, FIG. 4, above microparticles 90 shown stippled. |
| Outer | Mean light intensity in a predefined area in portions of the cassette outside of, and between, columns 82, FIG. 4. |
| PPos | Total area size of red blood cell agglutinates in a region encompassing the bottom portion of clear liquid 92, below the "Above", FIG. 5, and the upper portion of beads 90. Vertically, this is the region defined by thickness D1 and D2. Most preferably, D1 = 2 mm and D2 = 1 mm. |
| Zone1 | Total area size of red blood cell agglutinates that appear in the region marked "Zone1" as shown, FIG. 5. |
| Zone2 | Total area size of red blood cell agglutinates that appear in the region marked "Zone2" as shown, FIG. 5. |
| Zone3 | Total area size of red blood cell agglutinates that appear in the region marked "Zone3" as shown, FIG. 5. |
| PNeg | Size of red blood cell pellet, see FIG. 5. |

The PNeg portion is that portion which will contain a pellet 94 of non-agglutinated cells if any. As shown in FIG. 6, pellet 94 when imaged is assigned a "Slope", line 96, that is a best-fit straight line to the detected image of the upper surface 98 of the pellet. For convenience in compiling, "Slope" is expressed as an arc tangent value, namely in accordance with the equation:

"Slope"=1000 •tan(θ) where θ is the angle for line 96 as shown in FIG. 6 and 1000 is a factor used to make "slope" an integer value more easily handled by the computer. Line 96 in turn will deviate by a distance marked "Deviation", FIG. 6, when each pixel of the image is viewed, from the actual surface 98 in that pixel.

Figure 7:
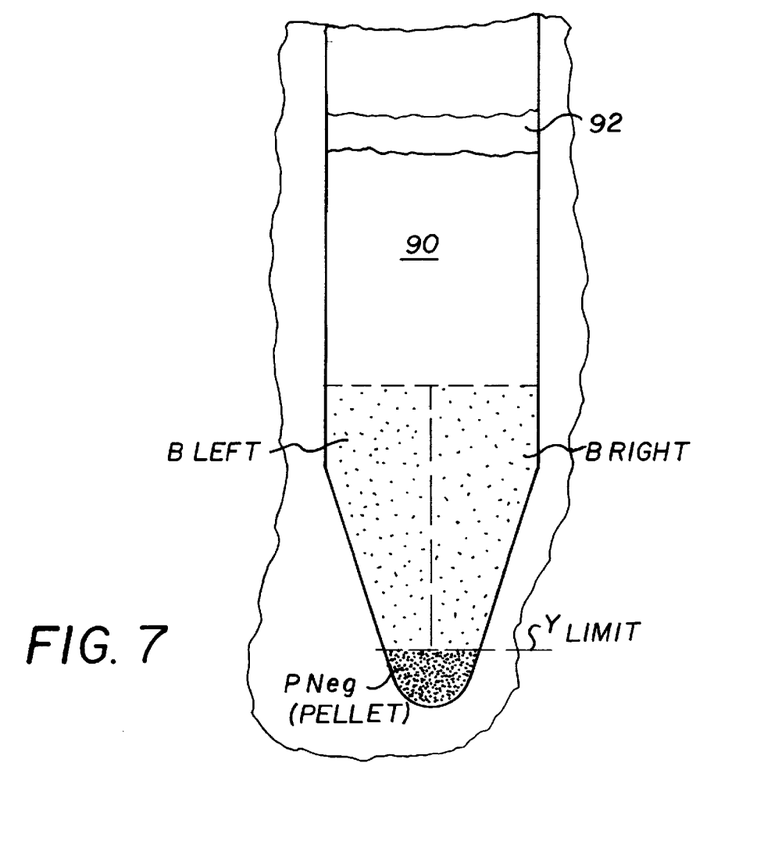
FIG. 7 is a fragmentary view similar to that of FIG. 5, but illustrating still further regions of the cassette identified in the process of the invention.

Still further, the bottom half of a column is divided up, FIG. 7, into a "B Left" region and "B Right" region.

In addition to the terms called out for FIGS. 4 through 7, there are other terms which are derivative terms, that need defining, as follows:

First of all, many of the intensity transmission measurements taken from the images are the summation of the results of the "Front" and "Back" images. "Front" and "Back" in turn mean, that each column is imaged twice— first with one side 81A, FIG. 3, facing the camera, and then with the other side 81B facing the camera. Which of these is in fact the "Front" is purely arbitrary, as long as the same convention is maintained throughout all cassettes.

Thus, as used herein, "AboveVar" is the sum of the "FrontAboveVar" and the "BackAboveVar", where either of these latter terms means, the liquid intensity variance for a front image of a column in the "Above" region, and such liquid intensity variance for a back image of a column in the above region, respectively. "Liquid Intensity Variance" in turn means, the root mean square deviation of actual intensities for each pixel, and more specifically, the value calculated by the formula:

$$\sqrt{\sum_{\substack{\text{all pixels} \\ \text{in the region} \\ \text{of interest}}} \frac{(I_{mean} - I_{actual})^2}{N}}$$

where $I_{mean}$ is the average intensity for all pixels in the region of interest, $I_{actual}$ is the actual intensity for a given pixel, and N equals the total number of pixels in the region of interest.

Also as used herein, "Resid" is the sum of "FrontResid" and "BackResid", wherein each of those is the root mean square of the deviation of line 96 from the actual pellet surface 98, FIG. 6, for each pixel, as measured by the formula:

$$\sqrt{\sum_{\substack{\text{all pixels in} \\ \text{the region of} \\ \text{interest}}} \frac{(\text{actual deviation for pixel})^2}{N}}$$

and as imaged from the Front and Back, respectively, as described above.

In summation, then, as disclosed in the '808 patent the procedure of reading a reaction includes steps of image acquisition, column detection, feature extraction and reaction grading. Images from both the front side and back side of the cassette are analyzed. After the completion of the image processing, the software routine outputs two sets of feature data associated to each well for the front and rear view. Before starting the classification, the two data sets from the front and back view are combined into one vector. The combination operation adds the same parameter of both views for each of the following major terms used in the calculations described hereinafter:

| | | | | |
|---|---|---|---|---|
| Above | = | FrontAbove | + | BackAbove |
| AboveVar | = | FrontAboveVar | + | BackAboveVar |
| Outer | = | FrontOuter | + | Backouter |
| PPos | = | FrontPPos | + | BackPPos |
| PNeg | = | FrontPNeg | + | BackPNeg |
| Zone1 | = | FrontZone1 | + | BackZone1 |
| Zone2 | = | FrontZone2 | + | BackZone2 |
| Zone3 | = | FrontZone3 | + | BackZone3 |
| Slope | = | FrontSlope | + | BackSlope |
| Resid | = | FrontResid | + | BackResid |
| BLeft | = | FrontBLeft | + | BackBRight |
| BRight | = | FrontBRight | + | BackBLeft |

The combined feature data are then used as inputs to the reaction classification routine which uses these values to determine whether an abnormality has occurred.

Abnormalities to be Detected

The following discussion concerns the specific abnormalities that are tested for, along with a statement of the calculations used to ascertain their presence, and the justification for those calculations. Although specific errors and specific calculations are preferred for detection, it will be readily apparent that others could also be utilized. For example, the numerical limitations are partly a function of the apparatus used, and any variations in apparatus can lead to variations in the numerical limitations that are readily ascertainable by one skilled in the art.

In general, the actual calculations were derived by producing artificially the noted abnormality in a number of cassettes, to a greater or lesser extent, or by selecting samples from patients known to have the condition, and then submitting those cassettes to experts to evaluate visually whether or not that particular column of that cassette evidenced that abnormality. Those cassettes ruled to be truly "abnormal" were then submitted to the signaling processing to ascertain what numerical limitations described below, had to be established to flag these abnormalities as being different from "normal" samples lacking these features.

For example: In the abnormality of "insufficient cells present", several columns were given to experts containing a variety of amounts of cells: 1 μL, 3 μL, 5 μL, 7 μL, and 10 μL, for example, where 10 μL is the nominal value. The experts determined that 3 μL and below was "too few" cells. The columns containing that amount were then processed and the algorithms (described below) adjusted so that only 3 μL and below were flagged.

The following then are the specific abnormalities detected:

Errors in Procedure Producing Out-Of-Range Data

Errors in test procedure or imaging could produce an image so irregular that it does not fit the database of images observed in "normal" samples. More specifically, such "out-of-range" images are likely to be in the distribution of detected cells in the column, and specifically, in left-to-right variances; and in the shape of any pellet of cells formed at the bottom of the column.

To determine an improper variance in left-to-right cell distribution, the computer calculates cell balance=|BLeft−BRight|. It then uses this new term, as well as the terms "Slope" and "Resid" defined above, within the following equation:

If (Cell Balance >3600) or (Slope >4500) or (Resid >2000), then the test is "out-of-range" and the reaction for that column ends.

The justification for this is as follows: There should not be a great disparity of cells, comparing "BLeft" with "BRight", FIG. 7. Any disparity giving a Cell Balance read-out of >3600 means that the image has never been encountered in "normal" samples of the database, and an error in processing must be presumed.

Alternatively, the pellet shape needs to be within certain parameters. "Slope >4500" means a slope where angle $\theta$, FIG. 6, is larger than 66°. "Resid >2000" means a deviation in surface 98 above or below line 96 that exceeds that which normally occurs. If either the "Slope" or the "Resid" (the deviation) is beyond these bounds, then the program halts to keep further classification steps from producing possible erroneous results.

Hemolysis of the Sample

As is well-known, hemolysis of red blood cells results in release of hemoglobin, which produces an overall reddening of the sample liquid not generally affected by the centrifuge step. It also reduces the volume of cells that can be imaged.

Accordingly, the signaling processing looks specifically at "Above", "Outer", "AboveVar", and also the computer calculates two derived terms":

One is "Ratio" which uses the formula: Ratio=Above/Outer.

The other is "Cell Volume", which uses the formula:
(A) Cell Vol.=PPos+PNeg+(Zone1+Zone2+Zone3)/3.

The equation used is as follows:
If (Ratio <0.75) and (Ratio•Cell Volume <1000) and (Cell Volume•AboveVar <20,000), then hemolysis is presumed, and the process of classifying the blood for type classes is ended due to this abnormality.

The justification is as follows: The hemoglobin will darken the liquid in the "Above" region, thus decreasing the detected intensity in that region. It will not, however, lessen the image intensity in the "Outer" region, FIG. 4. Hence the ratio measurement. Empirical testing as described above concerning the experts has produced a cut-off "Ratio" of 0.75.

This by itself is not enough due to the variation of optical density in plasma. True hemolysis will also reduce the Cell Volume. However, Cell Volume alone can vary due to normal variances of sample red cell concentration and volume originally added into the column. Furthermore, Cell Volume is not just the addition of all the imaged volumes, but preferably, it adds the average value for Zone1, Zone2, and Zone3 since those zones have been found to tend to otherwise contribute unduly to a count of cells. Thus, in applying the Cell Volume so defined to the algorithm, that processed number is multiplied by both the "Ratio" before checking against one empirically determined limit, and by "AboveVar" (liquid intensity variance) before checking against a second empirically determined limit. That is, it has been found that the liquid intensity variance must decrease, along with the "Ratio", before a drop in "Cell Volume" can be relied upon to be an accurate predictor of hemolysis. (A large liquid intensity variance is characteristic of conditions such as a blood clot, and hence the equation is set at less than 20,000.) And, it has been found that it is preferable that all three of the separate conditions of a decrease in Ratio, and a decrease in the product of Cell Volume and Ratio, and a decrease in the product of Cell Volume and liquid intensity variance, occur.

It will be appreciated that the hemolysis condition is not only an abnormality that can interfere with the normal testing, but also represents useful diagnostic information.

Empty Column Test

Conceptually, this test is a subset of "Insufficient Cells", described below. That is, that test will also trigger an abnormality flag if no cells whatsoever are present in the column, inasmuch as the test is set up to detect more than zero, but less than the cut-off (found to be 3 $\mu$L in a 10 $\mu$L nominal requirement.)

Insufficient/Too Many Cells Present

Insufficient sample or too much sample is obviously an error in the procedure. Both extremes need to be detected and eliminated. For this, the computer checks again the Cell Volume term as derived above for Hemolysis, and also calculates a modified Cell Volume' as follows: Cell Volume'=(PPos/2)+PNeg+(Zone1+Zone2 +Zone3)/3. It then conducts the following calculation:

If (Cell Volume <800), then there are Insufficient Cells present and the process of blood classification ends in that column.

If (Cell Volume'>7000), then there are too many cells present and the process of blood classification ends in that column.

As justification, the limits noted, and the use of Cell Volume', come from empirical testing. For some reason, PPos can be significantly large without necessarily being abnormal. Hence, the divisor of two is used.

Mixed Field Agglutination or Fibrin Test

Mixed field agglutination, hereinafter, simply "mixed field", is by far the most difficult abnormality to quantify, and thus to test for. In fact, it is so difficult that at present, it is not possible to distinguish in a flagged example between the presence of a mixed field and the presence of fibrin, other than to mechanically attempt to pull any fibrin off the top of the microparticles, thereby confirming that it is fibrin rather than a mixed field that is present.

As is understood in the art, a mixed field means that more than one type of blood classification is present. Examples would include a woman whose circulation contains fetal blood cells. Such blood will classify as a "mixed field". Blood banks diligently strive to eliminate potential donations of such blood, for obvious reasons. Hence, its detection is essential, and so important that even the fact that fibrin can produce the same result and yet be perfectly acceptable, is enough to stop the test and report that result.

The difficulty in detection is evident from the fact that, visually, a mixed field has somewhat the characteristics of several normal types of agglutination. In general, a "Mixed Field" is determined by the presence of too many cells at or near the top of the microparticles of the column, together with too many at the bottom of the column (where the pellet forms) and too few or insufficient cells detected at the portions of the column between said top of the microparticles and said bottom. This is understandable in that a normal +4 reaction produces a lot of cells agglutinated at or near said top, whereas a normal negative reaction produces a lot of non-agglutinated cells in the pellet at the bottom, and a normal +2 distributes the cells (some at the top, some at the bottom, and most importantly, some in between). Thus, any result that images a lot of cells at both the top and bottom, and not enough in between, is probably a mixed field.

Figure 8:
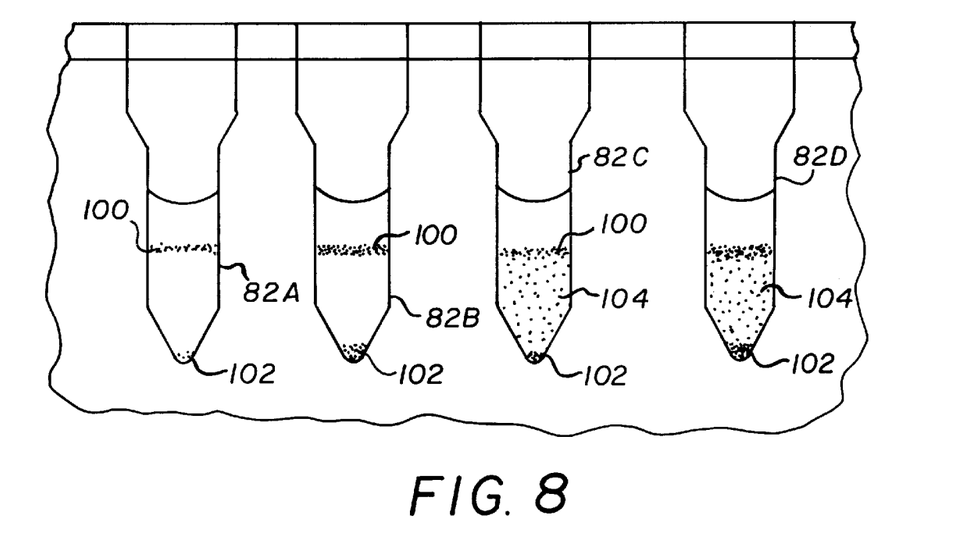
FIGS. 8–9 are fragmentary views of cassette columns as they actually appear when processed according to the invention, FIG. 8 being illustrative of mixed field agglutination and/or fibrin reaction.
Figure 9:
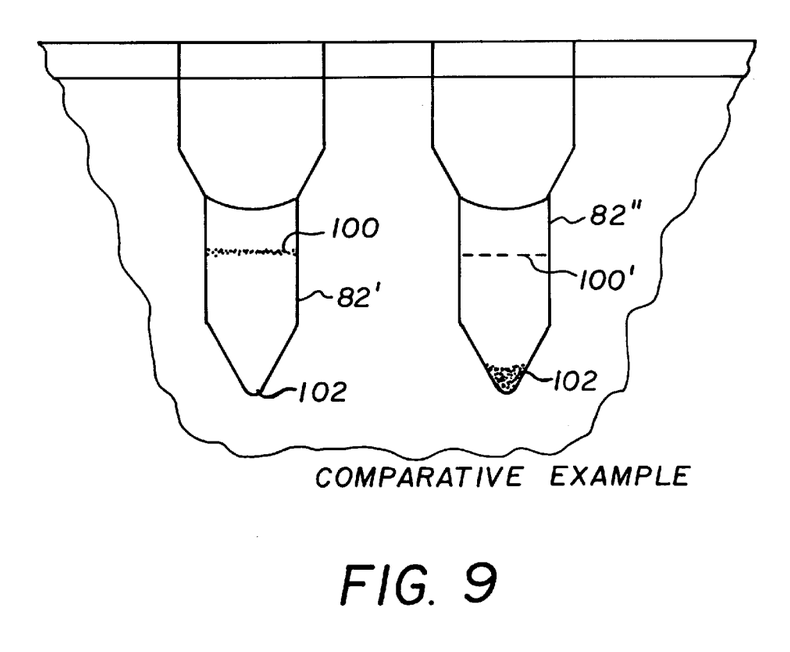

FIGS. 8 and 9 better illustrate the nature of the mixed field. More specifically, the wells 82 of FIG. 8 illustrate a range of mixed field reactions (or fibrin), whereas, by comparison the wells of 82 of FIG. 9 illustrate two "normal" reactions that bracket the range shown in FIG. 8.

Figure 4:
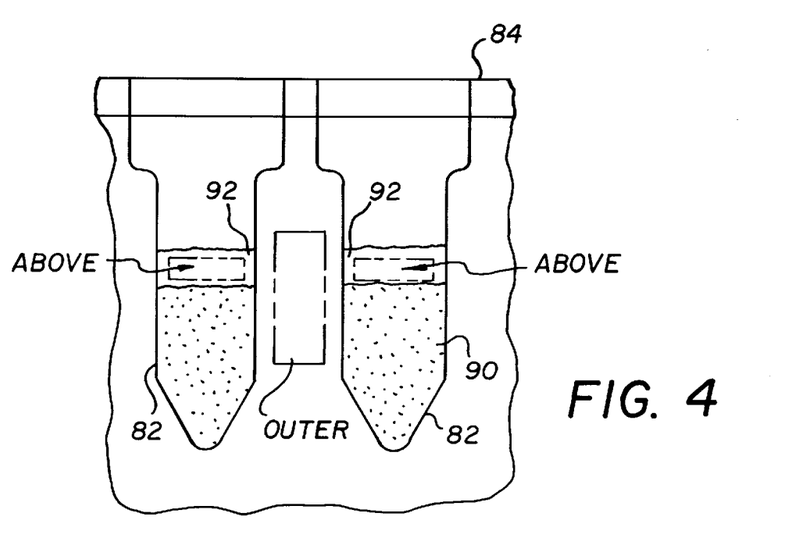
FIG. 4 is a fragmentary, partially schematic illustration of a portion of the cassette shown in FIG. 2, illustrating the location on the cassette of some of the regions identified in the process of the invention.

Thus, well 82A in FIG. 8 has a large amount of agglutinates collected at the PPos region 100, which is the top surface of the microparticles shown as portion 90 in FIG. 4. (The microparticles are not stippled in FIGS. 8 and 9, so that the blood cells can be identified.) What makes this well a mixed field is that there is also a small but significant PNeg collection at 102, of non-agglutinated cells. This then is a mixed field of +4, because of the image at 100, and of zero, because of the image at 102.

Well 82B is similar to 82A, the only difference being that the PNeg collection is very significant at 102, so that again the results are classified as a mixed field reaction of (4/0).

Figure 5:
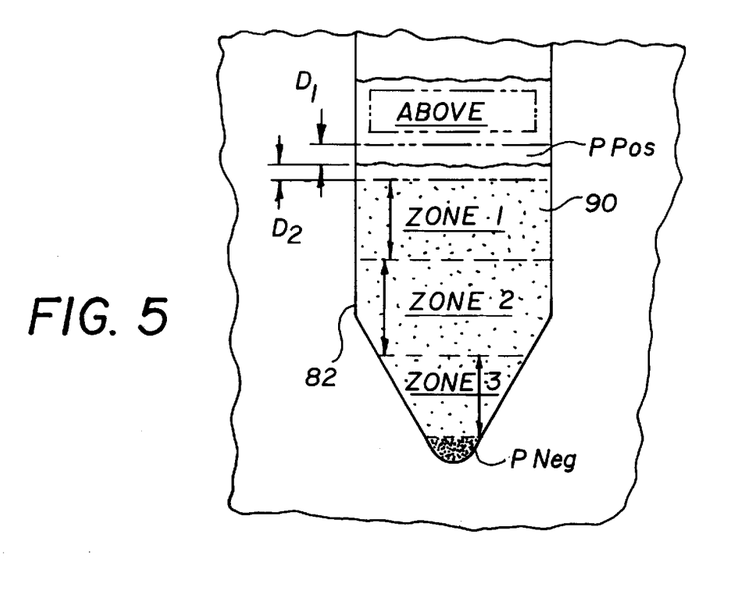
FIG. 5 is an enlarged fragmentary view of a single column of FIG. 4, showing the location of further regions of the cassette identified in the process of the invention.
Figure 6:
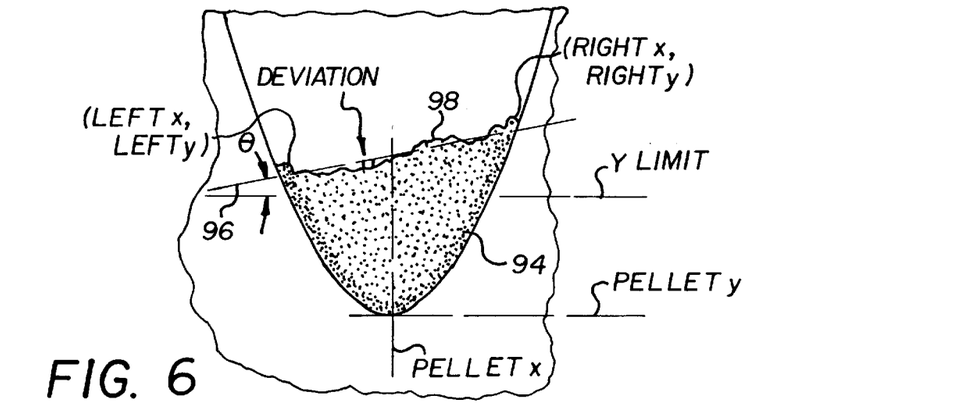
FIG. 6 is an enlarged fragmentary view of the bottom portion of the column of FIG. 5, with a pellet in the PNeg region, illustrating additional terms used in the process of the invention.

In wells 82C and 82D, for the first time, a distribution of small red blood cell agglutinates is seen in region 104 which covers Zone1, Zone2, and Zone 3 of FIG. 5, as well as at region 100 and 102 (PPos and PNeg). This distribution in region 104 indicates that the sample is +3, but the significant amount at PNeg (region 102) makes it also a zero classification—in other words, a mixed field reaction. (Well 82D differs from well 82C in that in 82D, the non-agglutinated collection at 102 is larger than in 82C.)

It will be appreciated that well 82B could also be an example of fibrin—that is, the dark appearance at region 100 could be caused by fibrin at the top of the microparticles in what is otherwise a zero classification reaction. In any event, neither a visual nor automated determination is capable of distinguishing whether it is a mixed field or fibrin.

By comparison, well 82' in FIG. 9 shows a normal +4 reaction, as indicated by the strong presence of agglutinates at region 100, and the absence of any significant cells at region 102 (PNeg). Compare this with well 82A of FIG. 8. Likewise, well 82" is a normal zero classification since all cells have centrifuged down to region 102. The dashed line at 100' in well 82" is present only to indicate where the top surface of the microparticles is located. There are no cells at 100'.

The method of this invention is able to distinguish all of the conditions of FIG. 8 as being abnormal and requiring termination of testing, as compared to the conditions shown in, e.g., FIG. 9.

Thus, to determine if either a mixed field or fibrin is present, the computer makes the following calculation:

(i) If (PNeg >300) and
(ii) (PPos >260) or (Zone1>1200) and
(iii) (Zone2<500) or (Zone<0.33•(PPos+Zone1) and Zone2<(1.5•PNeg)), then either a mixed field or fibrin is present, and classification using this column ends.

The justification is readily apparent for parts (i) and (ii) of the above calculation. That is, these two measure that both a large pellet is formed and a large agglutination is formed at the top. Part (iii) measures the absence of substantial cells in the middle, and for this, it has been found that the measure in Zone2 is most reliable. That is, if Zone2 is less than an absolute number or less than a fraction of the top portions (PPos and Zone1) of the microparticles, then it is suspect. But even then, Zone 2 is suspect only if its reduced content also is less than a constant (here, 1.5) times the pellet volume (PNeg).

As noted, a flag on this condition stops the classification that would otherwise proceed using this cassette column and the hardware and software of the '808 patent. However, as is true for all the abnormalities that are flagged by this invention, the user need not stop there. Alternatively, a new column can be used, in the same or a different cassette, to repeat the test on a fresh aliquot taken from the same supply of the blood in question. For example, in the case of a flag for "mixed field/fibrin", a retest might show no abnormal reaction, leading to the probable conclusion that the first result was due to fibrin. Unlike a "mixed field", if the condition was truly one of fibrin being present, there is no reason why the blood in question is not suitable for a blood bank.

EXAMPLES

The following working examples are non-exhaustive and presented solely to illustrate the embodiments described above. In each instance, a six column cassette available from Ortho Diagnostic Systems Inc. under the trademark "Ortho BioVue Systems" was tested using the apparatus and software described in the aforesaid '808 patent.

EXAMPLE 1

Hemolysis Reaction

A deliberately hemolyzed sample was inserted into an "Ortho BioVue" cassette for testing. Table II sets forth the actual intensity values that were detected.

TABLE II

| Feature | Front | Back |
| --- | --- | --- |
| Above | 79 | 82 |
| Outer | 238 | 238 |
| AboveVar | 4.57 | 6.42 |
| PPos | 0 | 4 |
| PNeg | 606 | 622 |
| Zone1 | 0 | 0 |
| Zone2 | 17 | 0 |
| Zone3 | 54 | 0 |
| Slope | 110 | 63 |
| Resid | 205 | 111 |
| BLeft | 86 | 37 |
| BRight | 159 | 51 |

From this, the "Ratio" was calculated to be:

(FrontAbove+BackAbove) / (FrontOuter+BackOuter) or (79+82) / (238+238)=161/476=0.338.

The Cell Volume (using formula (A) above)=(0+4)+(606+622)+ [(0+0)+(17+0)+(54+0)]/3, or 1232+71/3=1255.7.

AboveVar=FrontAboveVar+BackAboveVar=4.57+6.42=10.99

Since the test is whether Ratio <0.75 and Ratio•Cell Volume <1000 and Cell Volume•AboveVar <2000, the calculation turns out to be 0.338 is <0.75 and 0.338•1255.7≅424, is <1000 and 1255.7•10.99≅13,800, is <20,000.

Since all three conditions were met, the sample was flagged as being hemolytic.

EXAMPLE 2

Out-of-Range Features

The results of Example 1 can also be checked to determine if there were any out-of-range parameters as described above. To that end, Cell Balance was calculated as |(86+ 37)-(159+51)|, so that Cell Balance=87. The test for Cell Balance is, is it 73,600, and the answer is, no.

"Slope" is also checked to determine if "Slope" >4500. Here, Slope =110+63=173, and this is not >4500.

Finally, "Resid" is checked to see if Resid >2000. Here Resid=205+111, or 316, which is not >2000. This example is NOT out-of-range.

In the practice of the invention, the "out-of-range" test is conducted first, since if it is out-of-range, there is no need to, and the computer does not, conduct the hemolysis test.

EXAMPLE 3

Insufficient Cells

Example 1 was repeated, but this time too few cells were deposited, that is, a volume of only 3 µL was used. Table III sets forth the readings that were detected and calculations that resulted:

TABLE III

| Feature | Front | Back |
|---|---|---|
| PPos | 0 | 0 |
| PNeg | 313 | 435 |
| Zone1 | 0 | 8 |
| Zone2 | 6 | 16 |
| Zone3 | 0 | 0 |
| Slope | 27 | 16 |
| Resid | 43 | 36 |
| BLeft | 22 | 54 |
| BRight | 32 | 38 |

From this, the calculation for too few cells produced the result of: $[(0+0)+(313+435)+0.33] \cdot [(0+8)+(6+16)+(0+0)]$ which=758 and this indeed is <800. Hence, the results were flagged as "insufficient cells".

EXAMPLE 4

Too Many Cells

Example 1 was repeated, except that too many cells were deliberately added, by adding a volume of 50 μL. Table IV sets forth the readings detected and the calculations taken therefrom:

TABLE IV

| Feature | Front | Back |
|---|---|---|
| PPos | 0 | 0 |
| PNeg | 5365 | 4665 |
| Zone1 | 0 | 29 |
| Zone2 | 0 | 55 |
| Zone3 | 0 | 0 |
| Slope | 0 | 0 |
| Resid | 0 | 0 |
| BLeft | 0 | 0 |
| BRight | 0 | 0 |

Using the calculation for too many cells, one gets the result of $0.5 \cdot (0+0)+(5365+4665)+0.33 \cdot [(0+29)+(0+55)+(0+0)]$, or ≈10058 and indeed, this is >7000. Hence, this column was flagged as having too many cells.

EXAMPLE 5

Mixed Field Agglutination

Example 1 was repeated, except that the sample that was added was taken from patient samples known to have a mixed field reaction as determined visually by experts. Table V sets forth the results of the readings that were detected and calculations made therefrom:

TABLE V

| Feature | Front | Back |
|---|---|---|
| PPos | 868 | 644 |
| PNeg | 1381 | 1636 |
| Zone1 | 0 | 0 |
| Zone2 | 6 | 0 |
| Zone3 | 0 | 0 |
| Slope | 4 | 1 |
| Resid | 45 | 90 |
| BLeft | 79 | 252 |
| BRight | 100 | 276 |

From this, the calculation for "mixed field" was made as follows:
 (i) Is PNeg >300?
  That is, (1381+1636)≈3000,
  so that this is >300.
 (ii) Is (PPos >260) or (Zone1>1200)?
  That is, is 868+644 is greater than 260, even though 0+0 is not greater than 1200. Thus, the first of these is true.
 (iii) Is (Zone2<500) or is ((Zone2<0.33 (PPos+Zone1) and is Zone2<(1.5 Pneg))? That is, (6+0) is less than 500, so this is satisfied. Hence, all three of (i), (ii), and (iii) were satisfied, and the column was therefore flagged as having a mixed field.

Software

Figure 10:
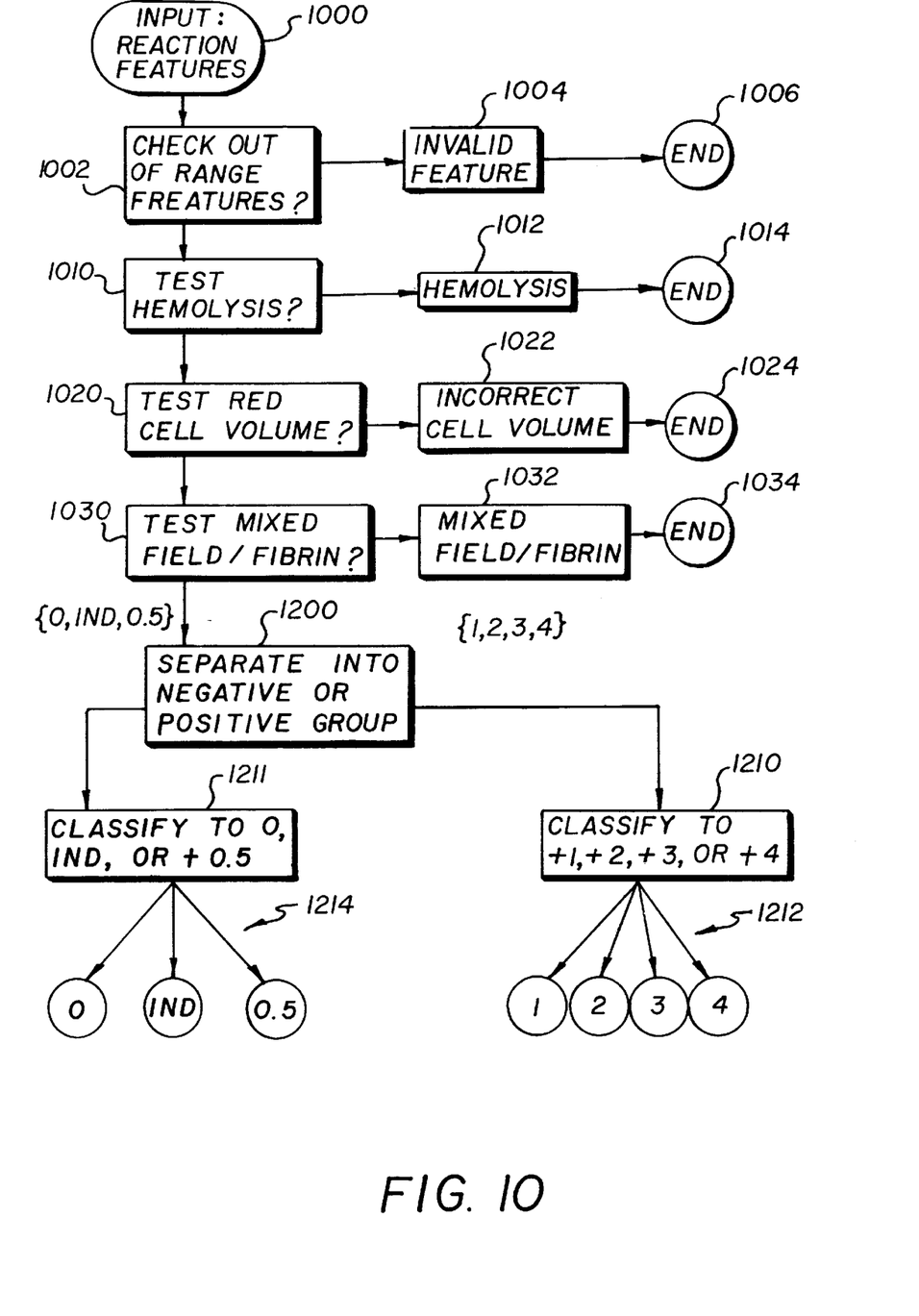
FIG. 10 is a flow chart of the steps of the invention and of the algorithm used to carry out the invention in a general purpose computer.

Conventional programming is used to program the computer, using such code as will achieve the steps of the flow chart of FIG. 10. (This can readily be achieved by as few as 200 lines of source code for steps 1002 through 1034.) That is, step 1000, the results taken from the imaging processing software as described in the '808 patent are inputted into the classification program in processor 60. Next, step 1002, the computer checks for processing errors producing out-of-range features of the column images, as described above. If one of these is detected, step 1004, the column is so flagged and that sample/column is not carried forward through any more calculations, step 1006. If no flag issues in the step 1004, the computer next checks for hemolysis, step 1010, as described above. If hemolysis is detected, the column is so flagged, step 1012, and the process ends on that column, step 1014.

Next, if still no flag has been issued, the computer tests for the red cell volume, step 1020, that is, is there either insufficient cell volume or too much, as described above? If either test turns out to be positive, a flag of incorrect cell volume is issued, step 1022 (which can also be more specific as to which it actually is), and the process ends on that column, step 1024.

If still no flag has issued, the computer next tests for mixed field/fibrin, as described above, step 1030. If this tests positive, then a flag is issued for that column, step 1032, and no further calculations are run on that column, step 1034.

Finally, assuming that all abnormalities test out as being "negative", the computer proceeds to the classification step 1200, which comprises determining if the sample is in the positive grouping 1210 or the "negative" grouping 1211. If it is in the positive grouping, it is then further classified as +1, +2, +3, or +4, step 1212, all as explained in the '808 patent. If it is in the "negative" grouping, this is further subclassified into known class zero, +0.5, or indeterminate, step 1214 shown as "Ind" in FIG. 10.

Thus, the computer preferably runs test 1002 before test 1010, before test 1020, which is before test 1030. The logic of doing test 1002 as the very first is readily apparent—if the results are out-of-range experimentally, no other test thereafter is valid. Also, test 1010 is preferably done before test 1020 or 1030 so that the hemolysis condition will be known even though the system might otherwise flag the sample as having insufficient cells. However, it is not essential that test 1020 be done before 1030.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method for detecting abnormal reactions in a cassette used for classifying red blood cell agglutination, the method comprising the steps of:
 a) inserting a patient blood sample into a cassette provided with agglutinating reagents and a column of microparticles;
 b) centrifuging the cassette to force non-agglutinated blood cells to flow through said column while retaining agglutinated cells at indicative locations in said column;
 c) producing on a detector array comprising a plurality of pixels, an image of said column and of blood cells distributed within and around said column;
 d) correlating the image on said array with predefined classes of images representing agglutination reactions of known classes; and
 e) prior to said step d), detecting the existence if any of an abnormality comprising errors in the processing of steps a), b) or c) that cause imaged features of the column or any pellet produced in the column to be out of range, wherein said errors comprise those represented by an abnormally large imbalance in the distribution of cells in said column when comparing one half of the column with the other half, or by an improperly shaped pellet of cells forced to the bottom of said column by said step b.

2. A method as defined in claim 1, wherein said improperly shaped pellet of abnormality i) is defined by the slope of a line fitted to the top surface of the pellet detected by said step c) and by the root mean square of the deviation between said fitted line and the real button surface.

3. A method for detecting abnormal reactions in a cassette used for classifying red blood cell agglutination, the method comprising the steps of:
 a) inserting a patient blood sample into a cassette provided with agglutinating reagents and a column of microparticles;
 b) centrifuging the cassette to force non-agglutinated blood cells to flow through said column while retaining agglutinated cells at indicative locations in said column;
 c) producing on a detector array comprising a plurality of pixels, an image of said column and of blood cells distributed within and around said column;
 d) correlating the image on said array with predefined classes of images representing agglutination reactions of known classes; and
 e) prior to said step d), detecting the existence if any of an abnormality in said produced image selected from the group consisting of:
  i) errors in the processing of steps a); b) or c) that cause imaged features of the column or any pellet produced in the column to be out of range;
  ii) hemolysis of the sample inserted in said step a);
  iii) insufficient or too many blood cells present in the cassette;
  iv) mixed field agglutination; and
  v) presence of fibrin at the top of said microparticles, wherein said step e) detects for the presence of each of said abnormalities i) through iii), and whether abnormality iv) or v) is present.

4. A method for detecting abnormal reactions in a cassette used for classifying red blood cell agglutination, the method comprising the steps of:
 a) inserting a patient blood sample into a cassette provided with agglutinating reagents and a column of microparticles;
 b) centrifuging the cassette to force non-agglutinated blood cells to flow through said column while retaining agglutinated cells at indicative locations in said column;
 c) producing on a detector array comprising a plurality of pixels, an image of said column and of blood cells distributed within and around said column;
 d) correlating the image on said array with predefined classes of images representing agglutination reactions of known classes; and
 e) prior to said step d), detecting the existence if any of an abnormality comprising hemolysis of the sample inserted in said step a), wherein said hemolysis is calculated by the ratio of intensity of liquid imaged inside the column above said microparticles and the intensity imaged in a predetermined area outside of said column, and by the cell volume and liquid intensity variance, wherein said variance is measured by the root-mean-square of the difference of the intensity value at each pixel from the average intensity value in the measuring area.

5. A method as defined in claim 4, wherein a factor in said calculation is that said ratio is less than 0.75.

6. A method as defined in claim 4 or 5, wherein said cell volume is calculated as the sum of cells imaged at the upper interface of the microparticles, the pellet if any at the bottom of the column, and the average of the cells detected in the regions between said upper interface and said pellet.

7. A method for detecting abnormal reactions in a cassette used for classifying red blood cell agglutination, the method comprising the steps of:
 a) inserting a patient blood sample into a cassette provided with agglutinating reagents and a column of microparticles;
 b) centrifuging the cassette to force non-agglutinated blood cells to flow through said column while retaining agglutinated cells at indicative locations in said column;
 c) producing on a detector array comprising a plurality of pixels, an image of said column and of blood cells distributed within and around said column;
 d) correlating the image on said array with predefined classes of images representing agglutination reactions of known classes; and
 e) prior to said step d), detecting the existence if any of an abnormality comprising insufficient or too many blood cells present in the cassette, wherein said step e) includes a detection of no blood sample in said column.

8. A method for detecting abnormal reactions in a cassette used for classifying red blood cell agglutination, the method comprising the steps of:
 a) inserting a patient blood sample into a cassette provided with agglutinating reagents and a column of microparticles;
 b) centrifuging the cassette to force non-agglutinated blood cells to flow through said column while retaining agglutinated cells at indicative locations in said column;
 c) producing on a detector array comprising a plurality of pixels an image of said column and of blood cells distributed within and around said column;
 d) correlating the image on said array with predefined classes of images representing agglutination reactions of known classes; and
 e) prior to said step d), detecting the existence if any of an abnormality in said produced image selected from the group consisting of:

i) mixed field agglutination; and ii) presence of fibrin at the top of said microparticles, wherein said abnormalities i) and ii) are together determined by the detection of too many cells present at or near the top of the microparticles of said column together with too many cells at the bottom of said column and insufficient cells detected at the portions of said column between said top and said bottom.

9. A method for detecting abnormal reactions in a cassette used for classifying red blood cell agglutination, the method comprising the steps of:

a) inserting a patient blood sample into a cassette provided with agglutinating reagents and a column of microparticles;

b) centrifuging the cassette to force non-agglutinated blood cells to flow through said column while retaining agglutinated cells at indicative locations in said column;

c) producing on a detector array comprising a plurality of pixels, an image of said column and of blood cells distributed within and around said column;

d) correlating the image on said array with predefined classes of images representing agglutination reactions of known classes; and e) prior to said step d), detecting the existence if any of an abnormality in said produced image selected from the group consisting of:

i) errors in the processing of steps a); b), or c) that cause imaged features of the column or any pellet produced in the column to be out of range;

ii) hemolysis of the sample inserted in said step a);

iii) insufficient or too many blood cells present in the cassette;

iv) mixed field agglutination; and v) presence of fibrin at the top of said microparticles, wherein the detection step e) tests in order for abnormalities i) through iii), followed by testing for either a mixed field or fibrin presence at the same time.

10. A method as defined in claim 1, 2, 3, 7, 8, or 9, wherein if said step e) detects any of said abnormalities, the method is halted before carrying out said step d).

11. A method as defined in claim 10, wherein if any of said abnormalities is detected, steps a) through e) are repeated on a fresh aliquot of the same blood sample in another column.

* * * * *